United States Patent
Burisch et al.

(10) Patent No.: US 9,121,796 B2
(45) Date of Patent: Sep. 1, 2015

(54) METHOD FOR EXECUTION UPON PROCESSING OF AT LEAST ONE HISTOLOGICAL SAMPLE

(71) Applicant: LEICA BIOSYSTEMS NUSSLOCH GMBH, Nussloch (DE)

(72) Inventors: Arne Burisch, Braunschweig (DE); Christian Löchte, Braunschweig (DE); Annika Raatz, Braunschweig (DE); Hermann Ulbrich, Bad Schoenborn (DE); Karl-Heinrich Westerhoff, Eppingen (DE)

(73) Assignee: LEICA BIOSYSTEMS NUSSLOCH GMBH, Nussloch (DE)

( * ) Notice: Subject to any disclaimer, the term of this patent is extended or adjusted under 35 U.S.C. 154(b) by 0 days.

(21) Appl. No.: 14/208,384

(22) Filed: Mar. 13, 2014

(65) Prior Publication Data
US 2014/0193314 A1 Jul. 10, 2014

Related U.S. Application Data

(63) Continuation of application No. 13/451,578, filed on Apr. 20, 2012, now Pat. No. 8,709,749.

(30) Foreign Application Priority Data

Apr. 20, 2011 (DE) .......................... 10 2011 002 196
Nov. 8, 2011 (DE) .......................... 10 2011 055 120

(51) Int. Cl.
*A61B 10/00* (2006.01)
*G01N 1/31* (2006.01)
*G01N 1/36* (2006.01)

(52) U.S. Cl.
CPC ... *G01N 1/31* (2013.01); *G01N 1/36* (2013.01)

(58) Field of Classification Search
CPC .................................. G01N 29/00; G01N 1/36
USPC ................................................ 422/536, 63–67
See application file for complete search history.

(56) References Cited

U.S. PATENT DOCUMENTS

| | | |
|---|---|---|
| 3,779,681 A | 12/1973 | Kinney et al. |
| 5,089,288 A | 2/1992 | Berger |
| 5,821,115 A | 10/1998 | Graupner |
| 6,207,408 B1 | 3/2001 | Essenfeld et al. |
| 7,547,538 B2 | 6/2009 | Morales et al. |
| 2010/0144002 A1 | 6/2010 | Donndelinger |
| 2010/0151513 A1 | 6/2010 | Vom et al. |
| 2010/0206226 A1 | 8/2010 | Ishii et al. |
| 2010/0248301 A1 | 9/2010 | Ulbrich et al. |
| 2010/0330660 A1 | 12/2010 | Hutchins et al. |

FOREIGN PATENT DOCUMENTS

| | | |
|---|---|---|
| DE | 4019182 | 1/1991 |
| DE | 60029129 | 11/2006 |
| DE | 102007022014 | 11/2008 |
| EP | 2184598 | 5/2010 |
| GB | 1396245 | 6/1975 |
| WO | 9909390 | 2/1999 |
| WO | 0144784 | 6/2001 |

*Primary Examiner* — Jyoti Nagpaul
(74) *Attorney, Agent, or Firm* — Hodgson Russ LLP

(57) ABSTRACT

The invention relates to a method for execution upon processing of at least one histological sample that is arranged, in particular after an infiltration process, in a closed cassette (2). The method is characterized in that prior to opening of the cassette (2), the sample is detached from the cover of the cassette (2) and/or isolated.

10 Claims, 2 Drawing Sheets

METHOD FOR EXECUTION UPON PROCESSING OF AT LEAST ONE HISTOLOGICAL SAMPLE

CROSS REFERENCE TO RELATED APPLICATIONS

Figure 1:
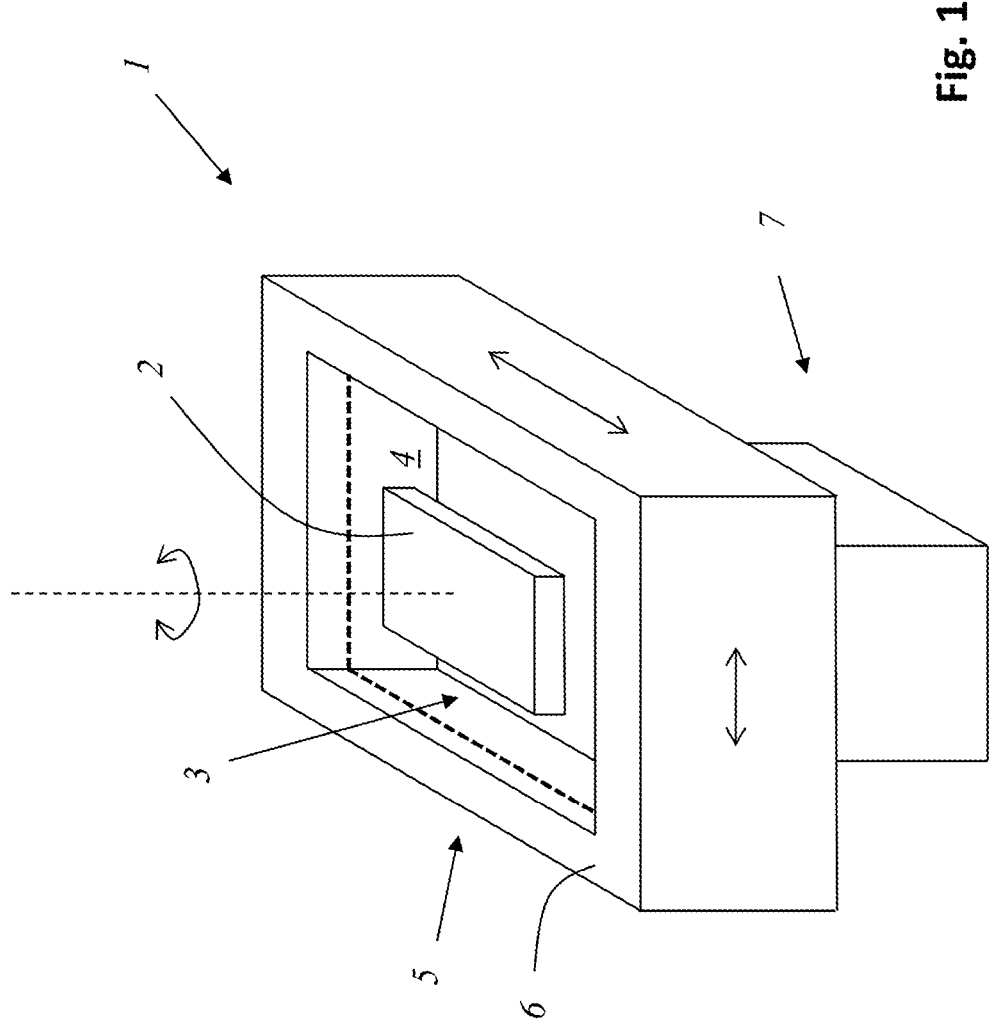

This application is a continuation application of U.S. Ser. No. 13/451,578, filed on Apr. 20, 2012, which in turn claims priority to German patent application number 10 2011 002 196.5 filed Apr. 20, 2011 and German patent application number 10 2011 055 120.4 filed Nov. 8, 2011, the entire disclosures of which are incorporated by reference herein.

FIELD OF THE INVENTION

The invention relates to a method for execution upon processing of at least one histological sample that is arranged, in particular after an infiltration process, in a closed cassette.

The invention further relates to an apparatus for treating at least one histological sample located in a cassette.

BACKGROUND OF THE INVENTION

In the context of the conditioning of histological samples, in particular in the preparation of histological samples in the context of an embedding process for later microtoming, they are firstly fixed by the application of various chemicals. The tissue liquid originally present in the natural cavities of the sample is thereby replaced, in multiple steps, by a fixing liquid, for example by formalin. In order to convert the fixed samples into a state that permits sectioning by means of a microtome, the fixing liquid is replaced by an embedding medium, for example paraffin, gelatin, agar, nitrocellulose, polyester wax, polyethylene glycol, or plastic. During the aforementioned processes, the samples are usually located in a cassette that comprises a plurality of sieve-like openings so that the chemicals can flow around the samples. A particular embodiment of such a cassette is known, for example, from DE 43 33 118 A1.

After infiltration of the embedding medium into the samples, the excess paraffin is drained off. After this step, the samples can be located anywhere within the cassette; because of the paraffin residues adhering to them, the samples as a rule adhere to the cassette cover, in the cassette cavity, and/or to one another. Stuck-together clumps of samples often form within the cassette.

Before further processing, in particular before automated, machine-controlled further processing, of the sample, for example before the further step of casting the samples into a paraffin block (called "blocking"), the sample or samples must be present in isolated fashion. Detachment and isolation can be performed, for example, using tweezers; disadvantageously, the risk exists that a sample may be damaged in this context and possibly even become unusable. In particular, the risk exists that changes which result in artifacts upon later analysis of tissue sections of the sample may be inadvertently caused to a sample.

DE 10 2007 022 014 A1 discloses a tissue embedding apparatus and a method for operating the same, which apparatus comprises a manipulation unit with which a sample inside the opened cassette can be transferred into a predefined position, orientation, and/or storage area.

EP 2 184 598 A1 discloses an apparatus for treating a tissue sample that comprises a bath for melted paraffin. An ultrasonic vibrator is provided for heating the bath.

DE 40 19 182 A1 discloses a method for impregnating tissue samples in paraffin. The method is notable for the fact that soaking of the tissue sample occurs in a closed, evacuated working space with ultrasound acting on the tissue sample and on the liquid paraffin surrounding said tissue sample. A similar method is known from US 2010/0144002 A1. According to this method, provision is made to apply infrasound or alternatively ultrasound in order to accelerate an infiltration process.

U.S. Pat. No. 6,207,408 B1 discloses a method for histological sample processing in which the sample is heated with the aid of microwaves during fixing, dehydration, and fat elimination.

US 2010/0151513 A1 discloses an apparatus and a method for sample handling and for embedding. According to the method, provision is made firstly to position a plurality of sample receptacles in an introduction apparatus, each sample receptacle having a mold associated with it; and then to convey the introduction apparatus into a wax bath. The introduction apparatus is then removed again from the wax bath and transferred to a cooling station in order to evaluate the wax.

It has become apparent that occasionally, despite every precaution, damage occurs to the sample or samples located in the cassette. The damage is usually manifested by the fact that the sample is torn or even ripped apart.

SUMMARY OF THE INVENTION

It is therefore the object of the present invention to describe a method for treating a sample located in a cassette, with which method the aforesaid damage can be avoided.

The object is achieved by way of a method which is characterized in that prior to opening of the cassette, the sample is detached from the cover of the cassette and/or isolated, the cassette with the at least one sample being heated before opening and in that context being exposed, directly or indirectly, to a mechanical vibration.

A further object of the present invention is to describe an apparatus that enables low-specimen-impact handling and removal of at least one histological sample located in a cassette.

The object is achieved by an apparatus which is suitable for detaching a sample, located in a closed cassette, from the inner side of the cover of the cassette, and/or for isolating the sample located in the closed cassette, without opening the cassette.

It has been recognized according to the present invention that the aforementioned damage to the samples is attributable to the fact that occasionally a sample adheres both to the inner side of the cover of the cassette and to the cassette basket, for example as a result of solidified paraffin. Upon opening of the cassette, i.e. upon separation of the cassette cover and cassette basket, a tensile stress occurs and ultimately, when the sample can no longer withstand the tensile stress, tearing or complete ripping of the sample occurs. In this case in particular, detachment according to the present invention from the cassette cover is especially appropriate in order to reduce stress on the sample.

Such damage can also occur if a sample is adhering on the one hand to the cassette cover and on the other hand to another sample that in turn is adhering to the cassette basket. It is likewise possible for the aforesaid damage to occur when a sample that is adhering directly or indirectly to the cassette basket also adheres directly or indirectly to the cassette cover. In this case in particular, isolation according to the present invention is especially appropriate in order to reduce stress on the sample.

The aforesaid damage can be entirely avoided, for example, by detaching the sample or samples located in the cassette from the cassette cover.

Alternatively or additionally, it is also possible for the sample to be isolated in such a way that at most it adheres either (directly or via another sample) to the cassette basket or (directly or via another sample) to the cassette cover.

Provision is made according to the present invention that the cassette having the at least one sample is heated upon detachment and/or isolation and in that context is exposed, directly or indirectly, to a mechanical vibration. In particular, the sample to be detached or isolated can in this fashion be shaken loose, for example, from the inner side of the cassette cover or from another sample.

The invention has the very particular advantage that detachment and/or isolation of the at least one sample, which is adhering to another sample or to the cassette as a result of, for example, solidified paraffin, can occur in entirely non-contact fashion. It is consequently not necessary according to the present invention (but is alternatively or additionally possible, if desired) to manipulate the sample with tools, for example tweezers. The risk of damaging the samples, or the risk of creating changes that later result in artifacts, is to that extent largely avoided. Irrespective thereof, detachment and/or isolation with the aid of tools coming directly into contact with the sample, in order to the carry out the method according to the present invention, is possible in principle, but is technically complex because of the small drain openings of usual cassettes.

In a particularly advantageous embodiment of the method according to the present invention, provision is made that for heating, the cassette is introduced into a heating bath having a liquid, in particular having liquid paraffin. The result thereby advantageously achieved is that the at least partly solidified embedding medium (usually paraffin), which causes adhesion of the at least one sample onto another sample or onto the inner side of the cassette, becomes melted. The result thereof is that the samples can easily be detached from one another and from inner walls of the cassette, in particular the cassette cover.

Particularly advantageously, provision can be made for the sample to be heated (directly or indirectly) by means of an oven and/or for the sample to be heated (directly or indirectly) by means of hot air and/or for the sample to be heated (directly or indirectly) by means of infrared radiation and/or for the sample to be heated (directly or indirectly) with microwave radiation and/or for the sample to be heated (directly or indirectly) by means of ultrasound.

In an embodiment in which the sample and/or the liquid of a heating bath is heated by impingement thereupon of a suitable vibration, for example by means of ultrasound or microwaves, provision can advantageously be made for the sample, in order to be shaken loose, to be exposed to an additional, further (in particular, mechanical) vibration.

An embodiment in which the cassette is arranged in a liquid, in particular in liquid paraffin, while vibration is being imparted is particularly advantageous. This embodiment ensures that the embedding medium that brings about adhesion of the at least one sample remains in the melted state while vibration is being generated. It is also conceivable, however, in a sequential procedure, firstly to bring about melting of the embedding medium and then to impart vibration to the cassette.

In a very particularly practical and easily implemented embodiment, provision is made that vibration is imparted to the liquid and/or to the vessel containing the liquid and/or to the sample receiving chamber containing the liquid. For example, vibration can be imparted to the liquid with the aid of a vibration generating means, such as e.g. a vibrator, arranged in the liquid. Provision can in particular be made according to the present invention for a vibration generating means to be positioned externally on a sample receiving chamber in which the cassette along with the sample is positioned, or externally on a vessel, for example a heating bath. In a particular embodiment, the sample receiving chamber and/or the vessel is positioned on the vibration generating means and/or carried thereby.

According to the present invention, any vibration mode is suitable in principle for executing the method. Provision can be made in particular for the vibration to contain a linear vibration and/or for the vibration to contain multiple vibrations of different vibration directions or different vibration modes. The vibration can in particular also contain a rotary vibration.

In a very particularly advantageous embodiment of the method according to the present invention, the sample is conveyed in controlled fashion, by the selection of the vibration mode and/or by the selection of the vibration amplitude and/or by the selection of the vibration frequency and/or by a definable or defined sequence of different vibrations, into a predefined and/or predefinable gripping position. In particular, the apparatus according to the present invention can comprise an open- or closed-loop control apparatus that controls the vibration mode and/or vibration amplitude and/or vibration frequency and/or a sequence of different vibrations, in open- or closed-loop fashion, in such a way that the sample moves into a predefined and/or predefinable gripping position. These embodiments have the very particular advantage that the sample thus conveyed into the gripping position can easily be removed from the cassette. In the context of such an embodiment, removal can In particular occur automatically and/or in machine-controlled fashion. Provision can be made in particular in this context for the gripper provided for removal always to travel to the same gripping position when a sample has been conveyed into that gripping position.

It is particularly advantageous and efficient if the vibration has a frequency between 100 Hz and 500 Hz. The vibration amplitude is preferably equal to 0.5 to 2 mm, in particular approx. 1 mm.

Especially with regard to automatic or completely automatic processing of histological samples, and very particularly with regard to an automated embedding process, provision can be made in a manner advantageous according to the present invention for detachment and/or isolation to proceed under the monitoring of an image processing system. Provision can be made in particular according to the present invention for the image processing system to operate automatically and independently. In a very particularly advantageous embodiment, detachment and/or isolation is automatically controlled in open- and/or closed-loop fashion, in particular by an open- or closed-loop control apparatus.

An embodiment in which an image processing system senses (preferably automatically) the position of the at least one sample or the position of multiple samples within the cassette, and forwards that information to an open- or closed-loop control apparatus, is very particularly advantageous. The open- or closed-loop control apparatus then regulates the vibration parameters, in particular a sequence of different vibration parameters, in such a way that a sample is in each case detached and is conveyed into a predefined and/or pre-definable gripping position. As soon as this has been accomplished, that fact is noted by the image processing system so that the open- or closed-loop control apparatus can then authorize further actions, for example temporary shutoff of the vibration and/or activation of the gripper in order to remove the sample.

As already mentioned, the vibration generating means can be embodied and arranged in order to impart vibration to the sample receiving chamber. With such an embodiment, the cassette and the samples is/are indirectly exposed to the vibration, in particular via a liquid located in the sample receiving chamber.

Alternatively or additionally, provision can also be made for vibration to be imparted to the cassette directly, and/or to a holder for the cassette. Provision can, for example, be made for this purpose for a vibration generating means to be arranged on a holder for the cassette and/or adjacently to a cassette.

In accordance with the method according to the present invention, the cassette can in a first step (before or during vibration generation) be fully submerged in a liquid (usually liquid paraffin) that is suitable for counteracting adhesion of the samples, in order to detach the at least one sample or the samples from the inner side of the cassette cover. This is appropriate in particular when the cassette cover is directed upward. In a subsequent step the cassette can, according to the present invention, be moved upward relative to the surface of the liquid (and/or the fill level can be lowered) sufficiently that the cassette cover can be opened with no risk of washing a sample away.

Opening of the cassette cover can also, advantageously, occur mechanically and/or automatically. After removal of the cassette cover, a further detachment of the samples from one another or from the inner sides of the cassette, in particular a dissolution of sample clumps, can occur by generation of vibration. This operation, too, can be monitored with the naked eye or with the aid of an image processing system, for example through one or more sieve openings of the cassette. Then, as already described, transfer of a sample into a predefined or predefinable gripping position, or transfer of multiple samples into multiple gripping positions, can occur.

The method according to the present invention and the apparatus according to the present invention have the very particular advantage that the samples located in the cassette can be gently prepared for automated removal despite adhesion and despite the formation of sample clumps.

Further objectives, advantages, features, and possible applications of the present invention are evident from the description below of an exemplifying embodiment with reference to the drawings. In this context, all the features described and/or graphically depicted, of themselves or in any useful combination, constitute the subject matter of the present invention, irrespective of their grouping in the claims or their internal references.

BRIEF DESCRIPTION OF THE DRAWING VIEWS

Figure 2:
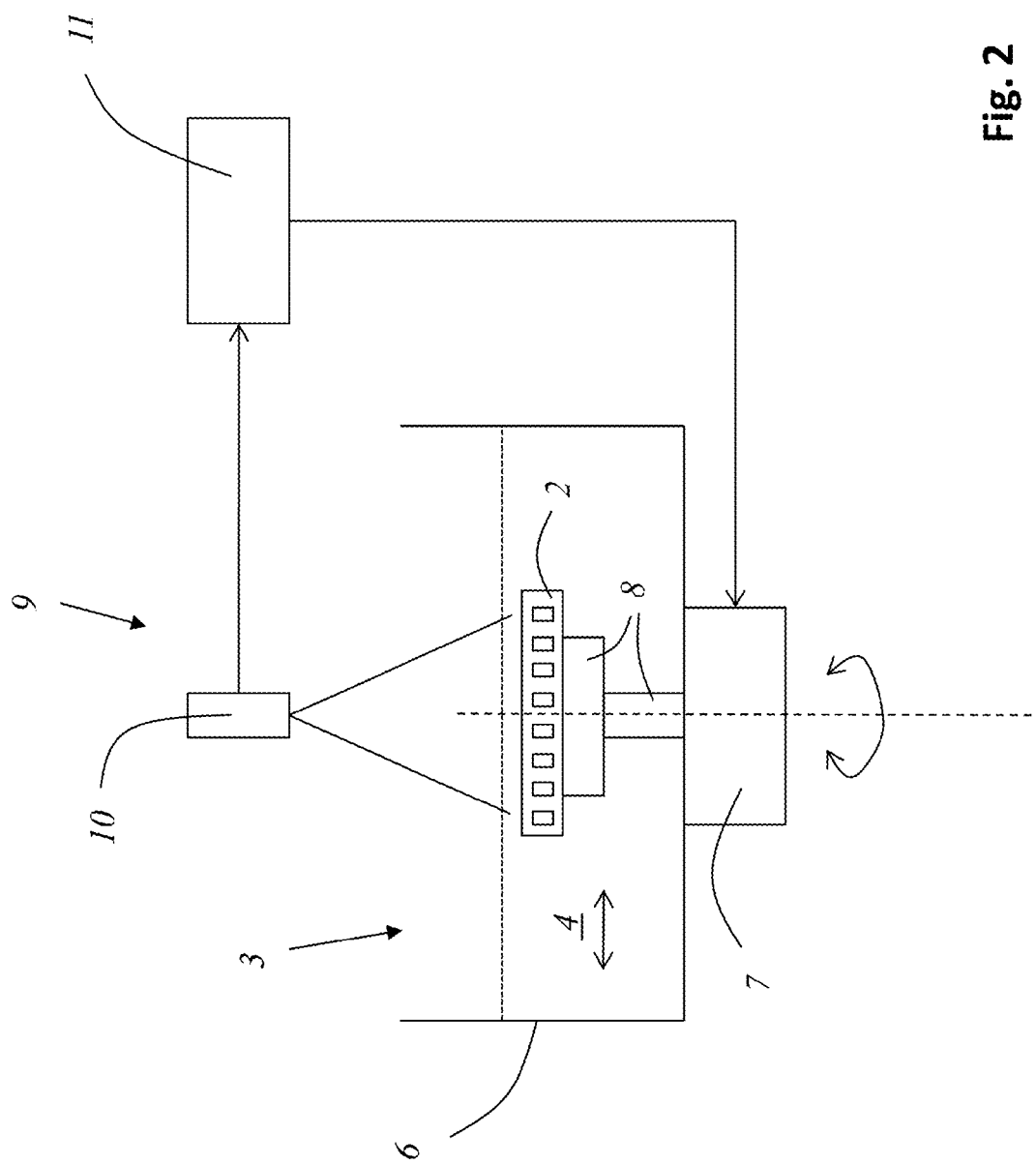

In the drawings:
FIG. 1 shows an apparatus according to the present invention, and
FIG. 2 shows another apparatus according to the present invention.

DETAILED DESCRIPTION OF THE INVENTION

FIG. 1 shows an apparatus 1 for treating at least one histological sample located in a closed cassette 2. Apparatus 1 is embodied and intended to detach the sample or samples located in the closed cassette 2, which are adhering (for example as a result of solidified paraffin) to one another or to the cassette, from the inner side of the cover of the cassette, and/or to isolate the sample located in the closed cassette 2.

The apparatus comprises a sample receiving chamber 3 that is filled with liquid paraffin 4. The edge of the surface of the liquid paraffin 4 is depicted with dashed lines in the Figures. Vessel 5 that makes available sample receiving chamber 3 is embodied as a heating bath 6. A heating film (not depicted) arranged beneath sample receiving chamber 3 serves to heat paraffin 4 and keep it liquid.

Heating bath 6 is arranged on vibration generating means 7 for generating a mechanical vibration, with which means a wide variety of vibration modes can be generated and can be transferred to the heating bath. In particular, the vibration generating means allows linear vibrations in a horizontal direction, and also the generation of a rotary vibration, as indicated by the corresponding double arrows in the Figure. It is also conceivable for the vibration generating means to generate a vibration in a vertical direction. Provision can be made in particular for the vibration parameters to be controlled in such a way that a respective sample can be shaken into a predefined and/or predefinable gripping position, for example by means of a particular sequence of different vibrations.

FIG. 2 shows a particular embodiment of an apparatus according to the present invention having a heating bath 6 that makes available a sample receiving chamber 3. A holder 8 for a cassette 2 is located in sample receiving chamber 3. Heating bath 6 is filled with liquid paraffin 4. A vibration generating means 7, which can comprise e.g. a vibrator or an eccentric-weight motor, is arranged beneath heating bath 6. Vibration can be imparted to heating bath 6 by means of vibration generating means 7, with the result that, by way of liquid 4 and holder 8, cassette 2 having the at least one sample is exposed to the vibration.

The apparatus comprises an image processing system 9 having a video camera 10 that optically monitors the operation of detachment and/or isolation through the sieve openings of the cassette cover of the closed cassette 2, and transmits monitoring signals to an open- and closed-loop control apparatus 11. Open- and closed-loop control apparatus 11 calculates, from the information obtained, which vibration and/or which vibration parameters are necessary in order to detach, isolate, and/or convey a sample sensed by image processing system 9 into a predefined gripping position, and regulates vibration generating means 7 accordingly.

PARTS LIST

1 Apparatus for treating histological samples
2 Cassette
3 Sample receiving chamber
4 Liquid
5 Vessel
6 Heating bath
7 Vibration generating means
8 Holder
9 Image processing system
10 Video camera
11 Open- and closed-loop control apparatus

What is claimed is:
1. An apparatus (1) for detaching and/or isolating at least one histological sample located in a cassette (2) closed by a cover, wherein the cassette (2) can be heated in the apparatus (1) before the cover is opened, wherein the apparatus (1) comprises:

a sample-receiving chamber (3) fillable with a liquid;

a holder (8) for the cassette (2), the holder (8) being mounted in the chamber; and vibration generating means (7) for generating mechanical vibrations and, prior to opening the cover, exposing the cassette (2) to vibration for detaching a sample, located in a closed cassette (2), from the inner side of the cover or for isolating the sample located in the closed cassette (2), without opening the cassette, wherein the vibration generating means (7) is operable to impart mechanical vibration to the cassette (2) via the holder (8).

2. The apparatus (1) according to claim 1, wherein the sample receiving chamber (3) is configured such that the cassette is immersible entirely into the liquid or the liquid level within the sample receiving chamber is raisable such that a previously introduced cassette is entirely immersed in the liquid.

3. The apparatus (1) according to claim 2, wherein the vibration generating means (7) is configured and arranged to impart vibration, directly or indirectly, to the liquid.

4. The apparatus (1) according to claim 3, wherein the vibration generating means comprises a vibrator placeable into the liquid or arranged in the liquid.

5. The apparatus (1) according to claim 1, wherein the vibration generating means (7) is configured and arranged to impart mechanical vibrations to the sample receiving chamber (3).

6. The apparatus (1) according to claim 1, wherein the sample receiving chamber (3) is part of a heating bath (6).

7. The apparatus (1) according to claim 1, wherein the vibration generating means (7) is controllable to select or adjust at least one of the following properties of the generated mechanical vibrations: amplitude, frequency, and sequence of different vibrations.

8. The apparatus (1) according to claim 7, further comprising an open- or closed-loop control apparatus (11) which controls the vibration generating means in open- or closed-loop fashion such that the sample is conveyed into a predefined gripping position.

9. The apparatus (1) according to claim 1, further comprising an image processing system (9) configured and arranged to monitor the detachment and/or isolation of the sample.

10. The apparatus (1) according to claim 9, further comprising an open- and/or closed-loop control apparatus (11) which controls the detachment and/or isolation in open- or closed-loop fashion based on information from the image processing system (9).

* * * * *